US00PP13789P29

(12) United States Plant Patent
Holtkamp, Sr.

(10) Patent No.: US PP13,789 P2
(45) Date of Patent: May 6, 2003

(54) AFRICAN VIOLET PLANT NAMED 'EVERPRAISE'

(75) Inventor: Reinhold Holtkamp, Sr., Nashville, TN (US)

(73) Assignee: International Plant Breeding AG, Liebefeld (CH)

( * ) Notice: Subject to any disclaimer, the term of this patent is extended or adjusted under 35 U.S.C. 154(b) by 0 days.

(21) Appl. No.: 10/046,985

(22) Filed: Jan. 17, 2002

(51) Int. Cl.[7] ..... A01H 5/00
(52) U.S. Cl. ..... Plt./270

(58) Field of Search ..... Plt./268, 267, 270

*Primary Examiner*—Kent Bell
(74) *Attorney, Agent, or Firm*—Foley & Lardner

(57) ABSTRACT

A new and distinct cultivar of African violet named 'EverPraise', as described and illustrated, and particularly characterized by the multiflorescense trait; single violet-shaped medium blue flowers with frilled greenish edge; strong, upright flower stems that curve slightly toward the center to form a compact flower bouquet above the leaves; medium green, wavy heart-shaped leaves; vigorous and extra large growth habit; flowering 12–13 weeks after potting, and long-lasting and non-dropping flowers.

1 Drawing Sheet

LATIN NAME OF THE GENUS AND SPECIES OF THE PLANT CLAIMED *sAINTPAULIA IONANTHA*.

VARIETY DENOMINATION

'EverPraise'.

BACKGROUND OF THE INVENTION

The present invention comprises a new and distinct cultivar of African Violet plant, botanically known as *Saintpaulia ionantha*, and hereinafter referred to by the cultivar name 'EverPraise'.

The new cultivar was referred to during the breeding and selection process by the designation 'R 7/1 A' and is a product of a planned breeding program. The new cultivar originated from a cross made by the inventor, Reinhold Holtkamp, Sr., in the controlled breeding program in Nashville, Tenn. The female, or seed parent, was a cultivar designated 'SB 4-2 muflo' (U.S. plant patent application Ser. No. 10/046,968). The male, or pollen parent was a cultivar designated 'P 6/6' (unpatented). 'SB 4-2 mulfo' was obtained from crosses made with plants derived from African Violet seeds stored on the space shutle for six years in a weightless environment on the Long Duration Exposure Facility.

In comparison to 'EverPraise', 'SB 4-2 muflo' is a cultivar having multiflorescent, single, violet-shaped medium blue flowers. The leaves of 'SB 4-2 muflo' are medium green, and in contrast to the leaves of 'EverPraise' are not wavy, nor crenate. Unlike 'EverPraise', the petals of 'SB 4-2 muflo' do not have the light green edge, and the flowers are not bi-colored. In comparison to 'EverPraise', 'P 6/6' is a cultivar having single, violet-shaped, non-multiflorescent, burgundy flowers. Similar to 'EverPraise', the petals of 'P 6/6'; have a light green edge.

'EverPraise' was discovered and selected by the inventor as a flowering plant within the progeny of the stated cross in a controlled environment in Nashville, Tenn. Asexual reproduction of the new cultivar by leaf cuttings, as performed by the inventor in Nashville, Tenn., has demonstrated that the combination of characteristics as herein disclosed for the new cultivar are firmly fixed and retained through successive generations of asexual reproduction. The new cultivar reproduces true-to-type.

'EverPraise' has not been observed under all possible environmental conditions. The phenotype may vary significantly with variations in environment such as temperature, light intensity and day-length without a change in genotype. The following observations, measurements and values describe the new cultivar as grown in Nashville, Tenn. and Haffen, Germany under greenhouse conditions which closely approximate those generally used in commercial practice.

BRIEF SUMMARY OF THE INVENTION

The following traits have been repeatedly observed and are determined to be basic characteristics of 'EverPraise', which in combination distinguish this African Violet as a new and distinct cultivar:

1) Multiflorescence characteristic;

2) A single crown as large as 35–45 cm in diameter;

3) Strong, upright flower stems curving slightly toward the center;

4) Single violet-shaped medium blue flowers with frilled greenish white edges;

5) Each plant carries 12–16, and sometimes more, upright flower stems each of which carries 12–16, and sometimes more, flowers;

6) Long lasting, non-dropping flowers;

7) vigorous and compact growth;

8) plant saleable 12–13 weeks after potting;

9) seed capsules visible above the petals;

10) medium green, wavy, heart-shaped leaves; and 11) after maturity the flowers dry off, and remain on the peduncle without becoming infected by botrytis.

The new cultivar is most similar to 'EverGrace' (U.S. plant patent application Ser. No. 10/046,747). Both 'EverPraise' and 'EverGrace' display the multiflorescence characteristic, have the same extra large growth habit and same type leaves and flower shape with the greenish edge. However, 'EverPraise' has medium blue flowers whereas 'EverGrace' has bi-colored white and medium blue flowers.

BRIEF DESCRIPTION OF THE DRAWING

The accompanying color photographic drawing shows a typical plant of the new cultivar 'EverPraise'. The colors appearing in the photographic drawing are as true as possible with color illustrations of this type. The photographic drawing is a top view of 'EverPraise' depicting the leaves and flowers.

DETAILED BOTANICAL DESCRIPTION

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn. Measurements were taken 16–18 weeks from potting, as grown in a 6" pot.

Parentage:

*Male parent.*—'P 6/6'.

*Female parent.*—'SB 4-2 muflo'.

Propagation: Leaf cuttings.

Plant: 12 cm to 14 cm tall when grown in pots, and 35–45 cm in diameter when fully grown.

*Leaves.*—General form: Heart-shaped. Leaf margin: Crenate. Apex: Emarginate.

*Size.*—95–105 mm wide and 100–115 mm long. Texture: Leatherlike. Aspect: Wavy, hairy, shiny. Veins: Upperside: visible, between RHS 147 A and RHS 147 B; underside: well pronounced, light green RHS 147 D with occasional touches of RHS 186 B, shiny. Color (upperside): Yellow-green RHS147 A. Color (underside): Greyed-green RHS 194 C to RHS 194D with touches of greyed-purple RHS 186 B. Petiole: Strong, light green RHS 147 C with occasional touches of RHS 187 A to RHS 183 A on underside; upperside between RHS 187 A and RHS 183 A, hairy.

*Flowers.*—Buds: Bell-shaped, light blue RHS 89 C with greenish RHS 145 C frilled edge visible, 8–10 mm in length, 7–8 mm in width just before opening. Sepals: Five (5), one for each flower petal, spear shaped, 4–6 mm in length, 1.5 to 2 mm in width at the base and 0.5 to 1 mm at the tips, margins are entire; upperside color: RHS 147 B to RHS 200 C, underside: RHS 147 B. Calyx: Shape: Funnel-shaped. Peduncle: Character: Strong upright, hairy; 20–25 mm in length, 1 mm in diameter; color purplish brown RHS 183 A and RHS 187 A.

*Individual flowers.*—Size: 35–40 mm in width (as measured when pressed flat), 30–35 mm in length (as measured from the top of the small petals to the bottom of the large middle petal). Shape: Single violet-shaped with finely frilled edges Petals: Violet-shaped, five (5 total, 3 large, 2 small); small petals are 12–14 mm in length and 10–13 mm in width; large petals are 18–22 mm in length and 15–18 mm in width; margins are wavy and finely filled; rounded apex shape. Color (upperside): Between violet-blue RHS 89 C and violet-blue RHS 94 A, with a very fine edge of yellow-green RHS 145 C. Occasionally, the green edge is lacking. Under cooler temperatures and more intensive lighting, the blue tends to intensify. Color (underside): Violet-blue RHS 89 D with fine edge of yellow-green RHS 145 C to RHS 145 D. Borne: Each flower stem carries 12–16 and more flowers on strong, upright peduncles that are free standing above the leaves, thereby forming a compact bouquet. Flowering habit: Flowers 12–13 weeks after potting Lastingness of the individual bloom: 4–6 weeks under good growing conditions.

*Reproductive organs.*—Stamens: Two (2): Anthers: 2 composed of 4 anther cells, seed capsules push slightly through. Pistil: One (1). Filaments: Yellowish white, 3–4 mm long. Pollen Color: Yellow RHS 7 A; moderate amount produced. Styles: 7–8 mm long, purplish blue, base of ovary light green and hairy.

*Roots.*—Normally developed, white when young, turning slightly brownish when older.

Disease resistance: Up to date, 'EverPraise' has shown very good resistance to all major violet diseases.

GENERAL OBSERVATIONS

'EverPraise' is a very attractive cultivar due to its abundance of medium blue flowers with frilled greenish white edges. Furthermore, 'EverPraise' is an outstanding cultivar due to the multiflorescence trait wherein the cultivar has 2 to 3 flower stems emerging out of each leaf internode, thereby giving the cultivar continuously new buds before the old flowers have wilted. A nice bouquet of free-standing flowers develop above the leaves 12–13 weeks after planting a rooted plantlet.

Under ideal growing conditions, 'EverPraise' is never without blooms. Each of the 12–16, or more, strong flower stems carries 12–16 and more single violet-shaped flowers with frilled edges. 'EverPraise' is an extra-large cultivar designed to be grown in a 15 cm pot. The plant may also be grown in a 10 cm pot successfully within a 8–10 week time period from potting to finish. The profuse flower bouquet is surrounded by large, medium green heart-shaped, wavy leaves. The flowers are long-lasting and non-dropping and the seed capsules push slightly through.

I claim:

1. A new and distinct African Violet plant named 'EverPraise', as described and illustrated herein.

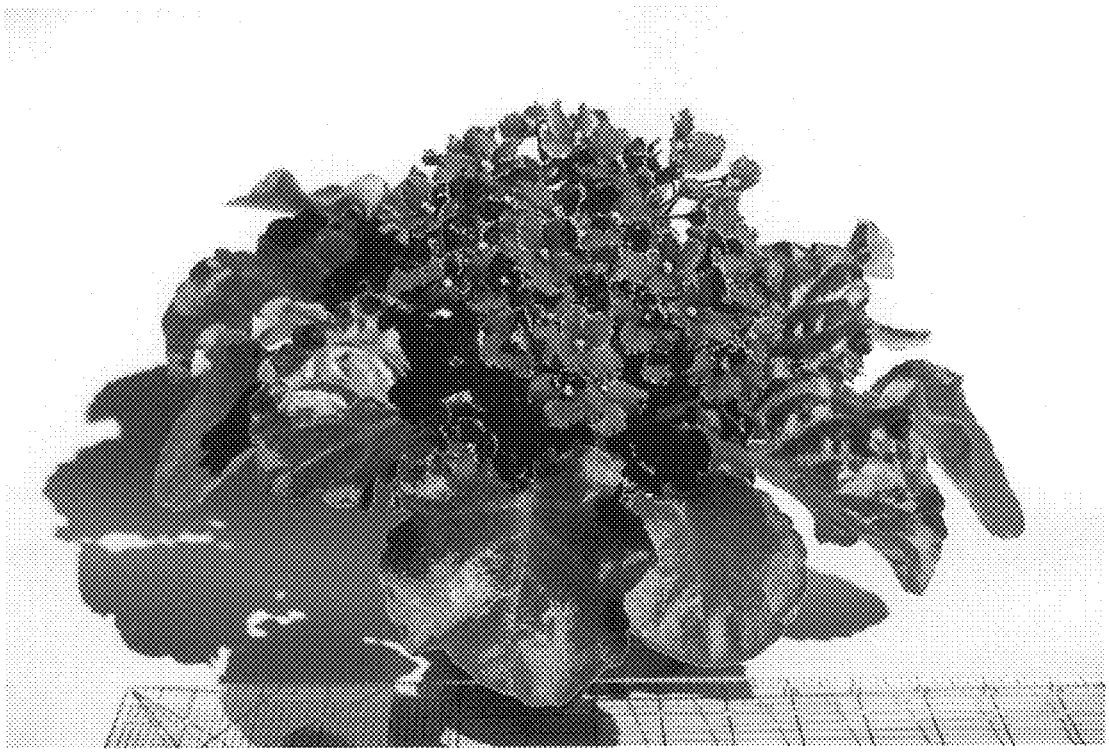

* * * * *